(12) United States Patent
Cole et al.

(10) Patent No.: US 7,294,287 B2
(45) Date of Patent: Nov. 13, 2007

(54) QUINOPHENANTHRINE DIONES FLUORESCENT WHITENING AGENTS

(75) Inventors: Damien Thurber Cole, Drexel Hill, PA (US); Kevin Rodney Gerzevske, Wilmington, DE (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 11/514,502

(22) Filed: Sep. 1, 2006

(65) Prior Publication Data

US 2007/0050927 A1 Mar. 8, 2007

Related U.S. Application Data

(60) Provisional application No. 60/714,810, filed on Sep. 7, 2005, provisional application No. 60/740,371, filed on Nov. 29, 2005.

(51) Int. Cl.
*C09K 11/06* (2006.01)
*C07D 471/02* (2006.01)

(52) U.S. Cl. ............ 252/301.21; 546/56; 546/57; 252/301.26

(58) Field of Classification Search ........... 546/56, 546/57; 252/301.21, 301.26
See application file for complete search history.

(56) References Cited

U.S. PATENT DOCUMENTS

| | | | |
|---|---|---|---|
| 4,969,350 A | 11/1990 | Fogal, Sr. | 73/40.7 |
| 5,308,545 A | 5/1994 | Meyer | 252/301.27 |
| 5,714,121 A | 2/1998 | Alderete et al. | 422/82.07 |
| 5,779,741 A | 7/1998 | Bacher et al. | 8/648 |
| 5,976,410 A | 11/1999 | Rohringer et al. | 252/301.21 |
| 6,054,021 A | 4/2000 | Kurrle et al. | 162/140 |
| 6,136,420 A | 10/2000 | Hibiya et al. | 428/213 |
| 6,174,586 B1 | 1/2001 | Peterson | 428/172 |
| 6,635,320 B2 | 10/2003 | Wakata et al. | 428/32.26 |
| 2005/0004362 A1 | 1/2005 | Huber et al. | 544/209 |
| 2006/0030707 A1 | 2/2006 | Cuesta et al. | 544/180 |

FOREIGN PATENT DOCUMENTS

WO 03/040240 5/2003

OTHER PUBLICATIONS

Jaydeep J. S. Lamba et al., Journal of the American Chemical Society, vol. 116, No. 26, pp. 11723-11736, (1994).

*Primary Examiner*—Charanjit S. Aulakh
(74) *Attorney, Agent, or Firm*—Joseph C. Suhadolnik

(57) ABSTRACT

Tetrahydro- and dihydroquinophenanthrine dione fluorescent whitening agents and a process for their preparation are provided.

19 Claims, No Drawings

QUINOPHENANTHRINE DIONES FLUORESCENT WHITENING AGENTS

This application claims benefit under 35 USC 119(e) of U.S. provisional application No. 60/714,810 filed Sep. 7, 2005 and 60/740,371 filed Nov. 29, 2005.

The present invention relates to tetrahydro- and dihydro-quinophenanthrine dione fluorescent whitening agents, the process for their preparation, their use as optical brighteners and light stabilizers in natural and synthetic materials and as fluorescent markers in applications such as defect detection, bio- and chemical assays and security printing.

BACKGROUND OF THE INVENTION

Fluorescent whitening agents (FWAs), also known as optical brighteners, have long been used in a wide variety of commercial applications such as paper, textiles, inks, coatings and plastics. By absorbing non-visible light in the UV range, then emitting the absorbed energy as visible light, notably visible blue light, FWAs provide a brighter appearance to materials into which they are formulated. For example, FWAs are used to camouflage a yellow or dingy color and create a whiter appearance in many paper and fabric applications and can mask slight discoloration in clear polymeric articles, for example clear polycarbonate.

Fluorescent whitening agents are also used to provide a brighter or more vibrant appearance to dyed and pigmented articles, as in textile, ink, coating and printing applications. Use in soaps, cosmetics and other personal care applications is also common.

Due to their ability to absorb light, particularly UV light, FWAs of sufficient permanence can also be useful as light screeners protecting both the material in which they are formulated as well as any light sensitive material deployed beneath, such as such as lower layers in a laminate, contents of a plastic bottle or even the skin under a clothing fabric into which a FWA has been incorporated. Certain FWAs, such as those of the present invention, can also slow light induced degradation by quenching the excited states generated upon light absorption of, for example, dyes and pigments.

FWAs have also found use in security printing, in bio- and chemical sensors and as markers allowing for the ready detection of defects in the manufacture and repair of a variety of articles including coated articles, electronic materials and even basic consumer products.

U.S. Pat. No. 5,976,410 discloses FWA dispersions used in coating paper or paper fibers in the pulp during paper production.

U.S. Pat. No. 5,308,545 discloses pyrazoline FWAs and their use in treating fabrics of natural, e.g., cellulose acetate, and synthetic fibers, e.g., acrylic, nylon. U.S. Pat. No. 5,779,741 discloses a method for the fluorescent whitening of cotton.

U.S. Pat. No. 6,635,320 discloses the use of FWAs in an ink jet recording sheet as both Ultra Violet absorber and optical brightener. U.S. Pat. No. 6,136,420 discloses laminated polyester film, useful as receiving media in printing, containing FWAs or FWAs and pigments.

U.S. Pat. Nos. 6,054,021 and 6,174,586 disclose the use of FWAs in security paper.

U.S. Pat. No. 5,714,121 discloses the use of FWAs in carbon dioxide sensors.

U.S. Pat. No. 5,976,410 discloses the use of fluorescent flavanoid derivatives in the production of easily inspected circuit boards and U.S. Pat. No. 4,969,350 discloses a method for inspecting tires for defects using solutions of commercially available FWAs.

Pending U.S. application Ser. No. 10/519,031, filed Jun. 23, 2006, discloses triazinylaminostilbene disulfonic acid mixtures, their use as FWAs in paper and textiles, and their use in fabrics to protect skin from UV radiation.

The above patents and application, and the references therein, are hereby incorporated in their entirety by reference.

A light absorbing para-terphenyl derivative (i.e., [4,3j] quinophenanthrine-6,13-dione) rendered rigid by the introduction of 2 fused lactam bridges linking the three phenyl rings is disclosed by Lamba and Tour, *J. Am. Chem. Soc.*, 1991, 116, 11723-11736.

DESCRIPTION OF THE INVENTION

This invention provides novel 5,7,12,14-tetrahydro[4,3-j] quinophenanthrine-6,13-diones and 5,12-dihydro[4,3-j] quinophenanthrine-6,13-diones, methods of their use, compositions containing them and the process whereby they are made.

The novel fluorescent whitening agents are compounds of formula (I) or (II)

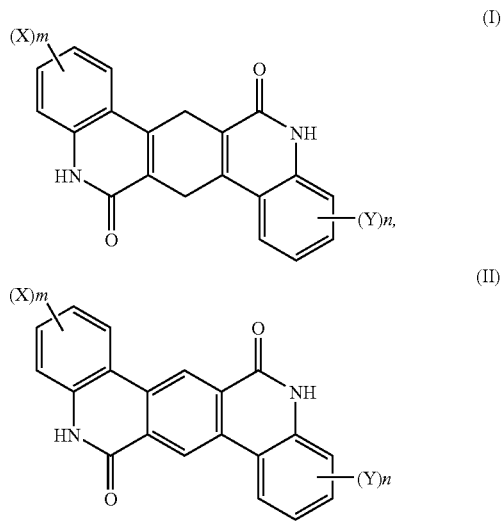

wherein

X and Y, independently of each other are $C_{1-12}$ straight or branched chain alkyl, $C_{3-6}$ cycloalkyl, $C_{6-10}$ aromatic, $C_{3-9}$ saturated or unsaturated heterocycle, $C_{7-12}$ aralkyl, halogen, —OR, $CF_3$, —COOR, —CONR'R, $NO_2$, NR'R, $SO_3H$, $SO_2NR'R$ or $C_{2-8}$-alkylcarbonyl, R and R', independently of each other are hydrogen, $C_{1-8}$ straight or branched chain alkyl, $C_{3-6}$ cycloalkyl, $C_{6-10}$ aromatic, $C_{7-12}$ aralkyl or $C_{2-8}$ alkylcarbonyl, and m and n are independently 0, 1, 2, 3 or 4, when m or n is 2, 3 or 4, each X or Y substituent may be a different group as defined above, with the proviso that in formula (II) m and n are not simultaneously 0.

For example, X and Y, independently of each other are $C_{1-8}$ straight or branched chain alkyl, $C_{5-6}$ cycloalkyl, $C_{6-10}$ aromatic, pyridine, $C_{7-12}$ aralkyl, halogen, —OR, $CF_3$, —COOR, —CONR'R, $NO_2$, NR'R, $SO_3H$ or $SO_2NR'R$, R and R', independently of each other are $C_{1-8}$ straight or branched chain alkyl, $C_{5-6}$ cycloalkyl, $C_{6-10}$ aromatic, $C_{7-12}$ aralkyl, acetyl or propionyl, and m and n are independently 0, 1 or 2, when m or n is 2 each X or Y substituent may be a different group as defined above.

For example, X and Y, independently of each other are F, Cl, Br, $C_{1-8}$ straight or branched chain alkyl, cyclohexyl, phenyl, naphthyl, benzyl, cumyl, —OH, $OC_{1-4}$ alkyl, $CF_3$, —$COOC_{1-8}$alkyl, —CONR'R, $NO_2$, NR'R or $SO_3H$, R and R', independently of each other are hydrogen, $C_{1-4}$ straight or branched chain alkyl, phenyl, benzyl or cumyl, and m and n are independently 0, 1 or 2, when m or n is 2 each X or Y substituent may be a different group as defined above.

For example, X and Y, independently of each other are F, Cl, Br, $C_{1-4}$ straight or branched chain alkyl, cyclohexyl, phenyl, naphthyl, benzyl, cumyl, —OH, $OC_{1-4}$ alkyl, $CF_3$, —$COOC_{1-4}$alkyl, —CONR'R, $NO_2$, NR'R or $SO_3H$, R and R', independently of each other are hydrogen or methyl and m and n are independently 0, 1 or 2, when m or n is 2 each X or Y substituent may be a different group as defined above.

For example, X and Y, independently of each other are Cl, $C_{1-4}$ straight or branched chain alkyl, $OC_{1-4}$ alkyl, and m and n are independently 0 or 1.

Straight or branched chain alkyl is a straight or branched chain of the specified number of carbon atoms and is for example methyl, ethyl, n-propyl, n-butyl, sec-butyl, tert-butyl, n-hexyl, n-octyl, 2-ethylhexyl, n-nonyl, n-decyl, n-undecyl or n-dodecyl.

$C_{3-9}$ saturated or unsaturated heterocycle is a cyclic moiety containing in the cycle from 3 to 9 carbon atoms and at least one heteroatom. Typical heteroatoms include O, S, N, Si, P. The heterocyle may be saturated, may contain one or more double bonds, may be aromatic and is optionally substituted or unsubstituted.

For example, the FWA is a compound of the following formulae

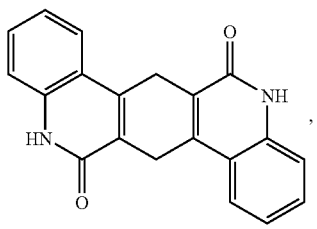,

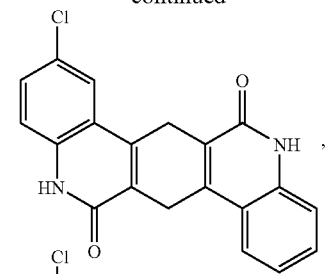,

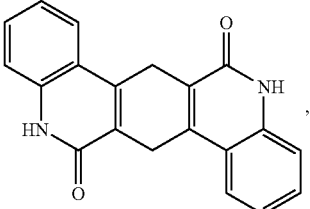,

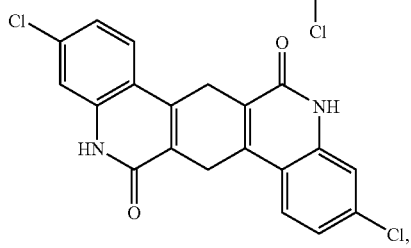,

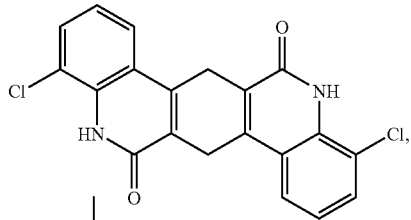,

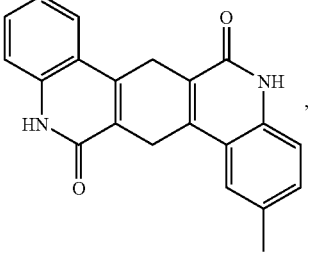,

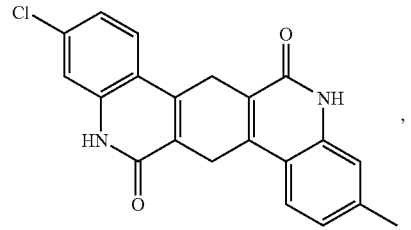,

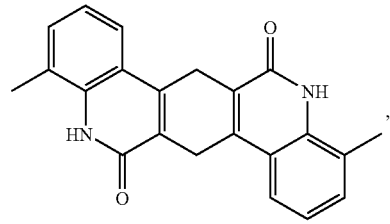,

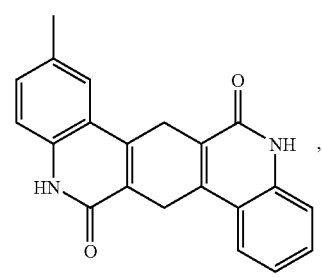

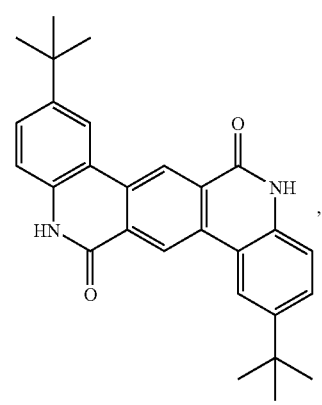

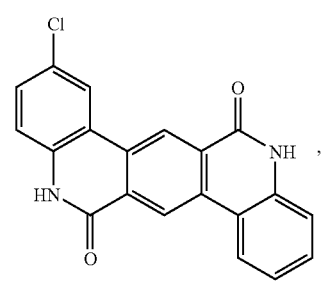

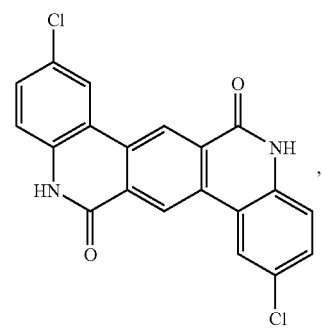

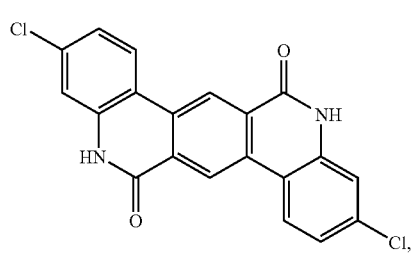

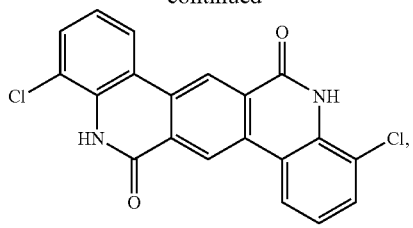

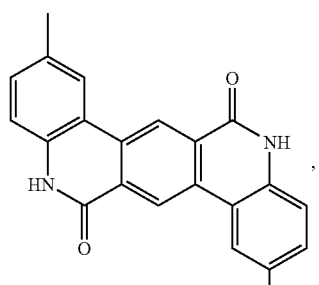

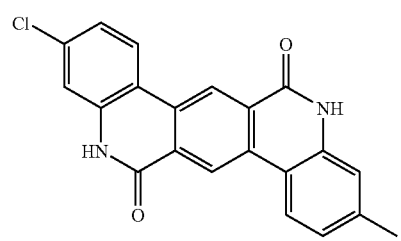

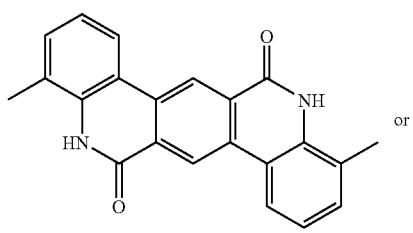

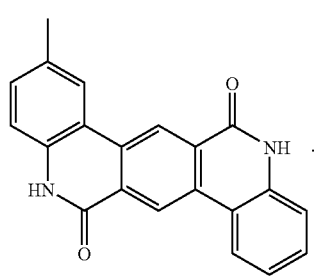

The compounds of the present invention are prepared by reaction of a succinic acid derivative, for example a di-$C_{1-12}$alkyl succinylsuccinate such as dimethyl succinylsuccinate, dioctyl succinylsuccinate or didodecyl succinylsuccinate, and an aniline derivative to form a dianiline amide of cyclohexane-1,4-dione-2,5-dicarboxylate which is cyclized and dehydrated to yield the desired tetrahydroquinophenanthrinedione.

Alternately, the dianiline amide of cyclohexane-1,4-dione-2,5-dicarboxylate is cyclized, dehydrated and aromatized to yield the desired dihydroquinophenanthrinedione.

The aniline used can be unsubstituted aniline, a substituted aniline, a mixture of unsubstituted aniline and one or more substituted anilines or a mixture of substituted anilines. The cyclization, dehydration and aromatization can be accomplished through a variety of known methods and can be accomplished in separate steps or through a one pot procedure.

The present invention also relates to ink, toner, polymer, cosmetic, home care, personal care and coating compositions comprising FWAs of formula (I) or (II) including compositions wherein the FWA is the compound of formula (II) where m and n are simultaneously 0.

The compounds of the present invention have limited solubility and form particles of various sizes in a manner similar to pigments. As such, further steps involving for example, grinding, milling and dispersion are anticipated. For example, the FWA particle can be ground to a very small size to improve coverage in a coating or other polymeric application. Various dispersants, for example, compounds commonly used in inks, paints and other coatings, may be used in suspensions of the FWA.

The FWAs of the present invention are thermally stable and can be processed at high temperatures, e.g., the temperatures used in processing polyamides, polyesters and polycarbonates.

In addition to being optical brighteners, the present compounds may be used as light stabilizers, luminescent markers or labeling agents, organic conductive materials and in other applications where fluorescence, energy transfer or electron transfer are advantageous.

As a luminescent marker, the FWAs of the present invention are, for example, used to verify paper articles and documents or to spot imperfections in manufacture.

For example, incorporation of the FWA into or onto paper fibers that become part of a paper during manufacture, or by applying the FWA to paper products as a coating in a distinctive pattern, yields a paper article, which upon exposure to UV light paper exhibits characteristic luminescence.

The FWAs can be used with dyes or pigments in security printing applications. For example, the FWA is incorporated into a toner or ink used to produce a printed article that is easily verified upon exposure to UV light by the luminescence of the printed portion providing quick identification, security and protection against forgery.

The FWA can also be used in applications wherein certain markings are made, for example, by a laser, on a finished article or a part of a finished article, which markings are not visible under ambient conditions, but become visible under specific circumstances, such as exposure to ultra violet light.

When added to a film forming polymer composition, such as a coating or masking agent, the presence of a small amount of the FWA in the composition provides a UV active marker to verify desired coverage of the coating or marker.

The FWAs of the present invention can be incorporated into or applied onto a wide variety of natural and synthetic materials, for example, polymeric materials including paper and other natural or synthetic polymers useful in a wide variety of applications including textiles, inks and other printing materials, coatings, molded articles, films including protective and functional films and packaging.

The FWAs of the present invention can be incorporated, for example, directly into or applied onto pigments, dyes, and formulations and dispersions comprising pigments and dyes.

The FWAs of the present invention are also useful in, for example cosmetic, cleaning, waxing, polishing, fabric care and personal care formulations.

As is evident from the previously cited patents which are incorporated by reference, many methods of incorporating FWAs are known and available in the art. These methods are applicable in the present case as well. Many other methods are also well known and are applicable in the use of the present FWAs.

Within the context of the present invention, paper, paper board, paper fibers and paper pulp should be understood as being an inherently crosslinked polymer, for example, in the form of cardboard, which can additionally be coated. Such substrates are, for example, commercially available.

Other natural polymers include cotton, viscose, flax, rayon, linen, wool, cashmere, angora, silk, cellulose, natural rubber, gelatin, or polymer-homologously chemically modified derivatives thereof, such as cellulose acetates, propionates and butyrates, the cellulose ethers such as methyl cellulose and also colophonium resins and derivatives.

Polymeric materials, or polymeric substrates, include thermoplastic, thermoset, elastomeric, inherently crosslinked or crosslinked polymers.

Examples of thermoplastic, thermoset, elastomeric, inherently crosslinked or crosslinked polymers are listed below.

1. Polymers of mono- and di-olefins, for example polypropylene, polyisobutylene, poly-butene-1, poly-4-methylpentene-1, polyisoprene or polybutadiene and also polymerisates of cyclo-olefins, for example of cyclopentene or norbornene; and also polyethylene (which may optionally be crosslinked), for example high density polyethylene (HDPE), high density polyethylene of high molecular weight (HDPE-HMW), high density polyethylene of ultra-high molecular weight (HDPE-UHMW), medium density polyethylene (MDPE), low density polyethylene (LDPE), and linear low density polyethylene (LLDPE), (VLDPE) and (ULDPE). Polyolefins, that is to say polymers of mono-olefins, as mentioned by way of example in the preceding paragraph, especially polyethylene and polypropylene, can be prepared by various processes, especially by the following methods:

a) by free radical polymerisation (usually at high pressure and high temperature);

b) by means of a catalyst, the catalyst usually containing one or more metals of group IVb, Vb, VIb or VIII. Those metals generally have one or more ligands, such as oxides, halides, alcoholates, esters, ethers, amines, alkyls, alkenyls and/or aryls, which may be either π- or σ-coordinated. Such metal complexes may be free or fixed to carriers, for example to activated magnesium chloride, titanium(II) chloride, aluminium oxide or silicon oxide. Such catalysts may be soluble or insoluble in the polymerisation medium. The catalysts can be active as such in the polymerisation or further activators may be used, for example metal alkyls, metal hydrides, metal alkyl halides, metal alkyl oxides or metal alkyl oxanes, the metals being elements of group(s) Ia, IIa and/or IIIa. The activators may have been modified, for example, with further ester, ether, amine or silyl ether groups.

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of mono- and di-olefins with one another or with other vinyl monomers, for example ethylene/propylene copolymers, linear low density polyethylene (LLDPE)

and mixtures thereof with low density polyethylene (LDPE), propylene/butene-1 copolymers, propylene/isobutylene copolymers, ethylene/butene-1 copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and copolymers thereof with carbon monoxide, or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another or with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers, LLDPE-ethylene/acrylic acid copolymers and alternately or randomly structured polyalkylene-carbon monoxide copolymers and mixtures thereof with other polymers, for example polyamides.

4. Hydrocarbon resins (for example $C_5$-$C_9$) including hydrogenated modifications thereof (for example tackifier resins) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate and methacrylate, styrene/maleic anhydride, styrene/acrylonitrile/methyl acrylate; high-impact-strength mixtures consisting of styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/-styrene.

7. Graft copolymers of styrene or a-methylstyrene, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleic acid imide on polybutadiene; styrene and maleic acid imide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under 6), such as those known, for example, as so-called ABS, MBS, ASA or AES polymers.

8. Halogen-containing polymers, for example polychloroprene, chlorinated rubber, chlorinated and brominated copolymer of isobutylene/isoprene (halobutyl rubber), chlorinated or chlorosulfonated polyethylene, copolymers of ethylene and chlorinated ethylene, epichlorohydrin homo- and co-polymers, especially polymers of halogen-containing vinyl compounds, for example polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.

9. Polymers derived from $\alpha,\beta$-unsaturated acids and derivatives thereof, such as poly-acrylates and polymethacrylates, or polymethyl methacrylates, polyacrylamides and poly-acrylonitriles impact-resistant-modified with butyl acrylate.

10. Copolymers of the monomers mentioned under 9) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers derived from unsaturated alcohols and amines or their acyl derivatives or acetals, such as polyvinyl alcohol, polyvinyl acetate, stearate, benzoate or maleate, poly-vinylbutyral, polyallyl phthalate, polyallylmelamine; and the copolymers thereof with olefins mentioned in Point 1.

12. Homo- and co-polymers of cyclic ethers, such as polyalkylene glycols, polyethylene oxide, polypropylene oxide or copolymers thereof with bisglycidyl ethers.

13. Polyacetals, such as polyoxymethylene, and also those polyoxymethylenes which contain comonomers, for example ethylene oxide; polyacetals modified with thermoplastic polyurethanes, acrylates or MBS.

14. Polyphenylene oxides and sulfides and mixtures thereof with styrene polymers or polyamides.

15. Polyurethanes derived from polyethers, polyesters and polybutadienes having terminal hydroxyl groups on the one hand and aliphatic or aromatic polyisocyanates on the other hand, and their initial products.

16. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides derived from m-xylene, diamine and adipic acid; polyamides prepared from hexamethylene-diamine and iso- and/or tere-phthalic acid and optionally an elastomer as modifier, for example poly-2,4, 4-trimethylhexamethylene terephthalamide or poly-m-phenylene isophthal-amide. Block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol. Also polyamides or copolyamides modified with EPDM or ABS; and polyamides condensed during processing ("RIM polyamide systems").

17. Polyureas, polyimides, polyamide imides, polyether imides, polyester imides, poly-hydantoins and polybenzimidazoles.

18. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, and also block polyether esters derived from polyethers with hydroxyl terminal groups; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, urea or melamine on the other hand, such as phenol-formaldehyde, urea-formaldehyde and melamine-formaldehyde resins.

22. Drying and non-drying alkyd resins.

23. Unsaturated polyester resins derived from copolyesters of saturated and unsaturated dicarboxylic acids with polyhydric alcohols, and also vinyl compounds as crosslinking agents, and also the halogen-containing, difficultly combustible modifications thereof.

24. Crosslinkable acrylic resins derived from substituted acrylic esters, e.g. from epoxy acrylates, urethane acrylates or polyester acrylates.

25. Alkyd resins, polyester resins and acrylate resins that are crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of bisphenol-A diglycidyl ethers, bisphenol-F diglycidyl ethers, that are crosslinked using customary hardeners, e.g. anhydrides or amines with or without accelerators.

27. Natural polymers, such as cellulose, natural rubber, gelatin, or polymer-homologously chemically modified derivatives thereof, such as cellulose acetates, propionates and butyrates, and the cellulose ethers, such as methyl cellulose; and also colophonium resins and derivatives.

28. Mixtures (polyblends) of the afore-mentioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The thermoplastic, crosslinked or inherently crosslinked polymer is, for example, a polyolefin, polyamide, polyurethane, polyacrylate, polyacrylamide, polyvinyl alcohol, polycarbonate, polystyrene, polyester, polyacetal or a halogenated vinyl polymer such as PVC.

The polymers may be, for example, in the form of films, injection-moulded articles, extruded workpieces, fibres, sheets, felts or woven fabrics.

The polymers may be, for example, polymers found in coatings such as in auto coatings, paints, stains, laminates, receiving layers for printing applications, or other protective or decorative coatings.

The polymer may be a substrate that, for example, can be used in the commercial printing area, sheet-fat- or web-printing, posters, calendars, forms, labels, wrapping foils, tapes, credit cards, furniture profiles, etc. The substrate is not restricted to the use in the non-food area. The substrate may also be, for example, a material for use in the field of nutrition, e.g. as packaging for foodstuffs, cosmetics, medicaments, etc.

The substrate, polymeric or otherwise, or formulation comprising the present FWAs may also optionally have incorporated therein or applied thereto other additives such as antioxidants, UV absorbers, hindered amines, phosphites or phosphonites, benzofuran-2-ones, thio-synergists, polyamide stabilizers, metal stearates, nucleating agents, fillers, reinforcing agents, lubricants, emulsifiers, dyes, pigments, dispersants, other optical brighteners, flame retardants, antistatic agents, blowing agents and the like, such as the materials listed below, or mixtures thereof.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-d i-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1-methylundec-1-yl)phenol, 2,4-di-methyl-6-(1-methylheptadec-1-yl)phenol, 2,4-dimethyl-6-(1-methyltridec-1-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl) disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3-tert-butyl-4-hydroxyphenyl) butyrate], bis(3-tert-butyl-4-hydroxy-5-methyl-phenyl)dicyclopentadiene, bis[2-(3'tert-butyl-2-hydroxy-5-methylbenzyl)-6-tert-butyl-4-methylphenyl]terephthalate, 1,1-bis-(3, 5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1, 5,5-tetra-(5-tert-butyl-4-hydroxy-2-methylphenyl)pentane.

1.7. Benzyl compounds, for example 3,5,3',5'-tetra-tert-butyl-4,4'-dihydroxydibenzyl ether, octadecyl-4-hydroxy-3, 5-dimethylbenzylmercaptoacetate, tridecyl-4-hydroxy-3,5-di-tert-butylbenzylmercaptoacetate, tris(3,5-di-tert-butyl-4-hydroxybenzyl)amine, 1,3,5-tri-(3,5-di-tert-butyl-4-hydroxybenzyl)-2,4,6-trimethylbenzene, di-(3,5-di-tert-butyl-4-hydroxybenzyl)sulfide, 3,5-di-tert-butyl-4-hydroxybenzyl-mercapto-acetic acid isooctyl ester, bis-(4-tert-butyl-3-hydroxy-2,6-dimethylbenzyl)dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl)isocyanurate, 3,5-di-tert-butyl-4-hydroxybenzyl-phosphoric acid dioctadecyl ester and 3,5-di-tert-butyl-4-hydroxybenzyl-phosphoric acid monoethyl ester, calcium-salt.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-ditert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxy-lauric acid anilide, 4-hydroxy-stearic acid anilide, 2,4-bis-octylmercapto-6-(3,5-tert-butyl-4-hydroxyanilino)-s-triazine and octyl-N-(3,5-di-tert-butyl-4-hydroxyphenyl)-carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl] propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenylamino)propane, (o-tolyl)biguanide, bis[4-( 1',3'-dimethylbutyl)phenyl]amine, tert-octylated N-phenyl-1-naphthylamine, a mixture of mono- and dialkylated tert-butyl/tert-octyl-diphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilizers 2.1. 2-(2-Hydroxyphenyl)-2H-benzotriazoles, for example known commercial hydroxyphenyl-2H-benzotriazoles and benzotriazoles as disclosed in, U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905, 4,853,471; 5,268,450; 5,278,314; 5,280,124; 5,319,091; 5,410,071; 5,436,349; 5,516,914; 5,554,760; 5,563,242; 5,574,166; 5,607,987 and 5,977,219, such as 2-(2-hydroxy-5-methylphenyl)-2H-benzotriazole, 2-(3,5-di-t-butyl-2-hydroxyphenyl)-2H-benzotriazole, 2-(2-hydroxy-5-t-butylphenyl)-2H-benzotriazole, 2-(2-hydroxy-5-t-octylphenyl)-2H-benzotriazole, 5-chloro-2-(3,5-di-t-butyl-2- hydroxyphenyl)-2H-benzotriazole, 5-chloro-2-(3-t-butyl-2-hydroxy-5-methylphenyl)-2H-benzotriazole, 2-(3-sec-butyl-5-t-butyl-2-hydroxyphenyl)-2H-benzotriazole, 2-(2-hydroxy-4-octyloxyphenyl)-2H-benzotriazole, 2-(3,5-di-t-amyl-2-hydroxyphenyl)-2H-benzotriazole, 2-(3,5-bis-α-cumyl-2-hydroxyphenyl)-2H-benzotriazole, 2-(3-t-butyl-2-hydroxy-5-(2-(ω-hydroxy-octa-(ethyleneoxy)carbonyl-ethyl)-, phenyl)-2H-benzotriazole, 2-(3-dodecyl-2-hydroxy-5-methylphenyl)-2H-benzotriazole, 2-(3-t-butyl-2-hydroxy-5-(2-octyloxycarbonyl)ethylphenyl)-2H-benzotriazole, dodecylated 2-(2-hydroxy-5-methylphenyl)-2H-benzotriazole, 2-(3-t-butyl-2-hydroxy-5-(2-octyloxycarbonylethyl)phenyl)-5-chloro-2H-benzotriazole, 2-(3-tert-butyl-5-(2-(2-ethylhexyloxy)-carbonylethyl)-2-hydroxyphenyl)-5-chloro-2H-benzotriazole, 2-(3-t-butyl-2-hydroxy-5-(2-methoxycarbonylethyl)phenyl)-5-chloro-2H-benzotriazole, 2-(3-t-butyl-2-hydroxy-5-(2-methoxycarbonylethyl)phenyl)-2H-benzotriazole, 2-(3-t-butyl-5-(2-(2-ethylhexyloxy)carbonylethyl)-2-hydroxyphenyl)-2H-benzotriazole, 2-(3-t-butyl-2-hydroxy-5-(2-isooctyloxycarbonylethyl)phenyl-2H-benzotriazole, 2,2'-methylene-bis(4-t-octyl-(6-2H-benzotriazol-2-yl)phenol), 2-(2-hydroxy-3-α-cumyl-5-t-octylphenyl)-2H-benzotriazole, 2-(2-hydroxy-3-t-octyl-5-α-cumylphenyl)-2H-benzotriazole, 5-fluoro-2-(2-hydroxy-3,5-di-α-cumyl-phenyl)-2H-benzotriazole, 5-chloro-2-(2-hydroxy-3,5-di-α-cumylphenyl)-2H-benzotriazole, 5-chloro-2-(2-hydroxy-3-α-cumyl-5-t-octylphenyl)-2H-benzotriazole, 2-(3-t-butyl-2-hydroxy-5-(2-isooctyloxycarbonylethyl)phenyl)-5-chloro-2H-benzotriazole, 5-trifluoromethyl-2-(2-hydroxy-3-α-cumyl-5-t-octylphenyl)-2H-benzotriazole, 5-trifluoromethyl-2-(2-hydroxy-5-t-octylphenyl)-2H-benzotriazole, 5-trifluoromethyl-2-(2-hydroxy-3,5-di-t-octylphenyl)-2H-benzotriazole, methyl 3-(5-trifluoromethyl-2H-benzotriazol-2-yl)-5-t-butyl-4-hydroxyhydrocinnamate, 5-butylsulfonyl-2-(2-hydroxy-3-α-cumyl-5-t-octylphenyl)-2H-benzotriazole, 5-trifluoromethyl-2-(2-hydroxy-3-α-cumyl-5-t-butylphenyl)-2H-benzotriazole, 5-trifluoromethyl-2-(2-hydroxy-3,5-di-t-butylphenyl)-2H-benzotriazole, 5-trifluoromethyl-2-(2-hydroxy-3,5-di-α-cumylphenyl)-2H-benzotriazole, 5-butylsulfonyl-2-(2-hydroxy-3,5-di-t-butylphenyl)-2H-benzotriazole and 5-phenylsulfonyl-2-(2-hydroxy-3,5-di-t-butylphenyl)-2H-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates and malonates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline, dimethyl p-methoxybenzylidenemalonate (CAS#7443-25-6), and di-(1,2,2,6,6-pentamethylpiperidin-4-yl) p-methoxybenzylidenemalonate (CAS #147783-69-5).

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amine stabilizers, for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl) sebacate, bis(2,2,6,6-tetramethyl-4-piperidyl) succinate, bis(1,2,2,6,6-pentamethyl-4-piperidyl) sebacate, bis( 1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethyl-piperidyl)succinate, linear or cyclic condensates of N,N'-bis-(2,2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

The sterically hindered amine may also be one of the compounds described in GB-A-2301106 as component I-a), I-b), I-c), I-d), I-e), I-f), I-g), I-h), I-i), I-j), I-k) or I-l), in particular the light stabilizer 1-a-1, I -a-2, 1-b-1, 1-c-1, 1-c-2, 1-d-1, 1-d-2, 1-d-3, 1-e-1, 1-f-1, 1-g-1, 1-g-2 or 1-k-1 listed on pages 68 to 73 of said GB-A-2301106.

The sterically hindered amine may also be one of the compounds described in EP 782994, for example compounds as described in claims 10 or 38 or in Examples 1-12 or D-1 to D-5 therein.

The sterically hindered amine may also be a hydroxylamine, hydroxylamine salt or nitroxl derivative of hindered amine light stabilizers.

2.7. Sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethyl-piperidin-4-yl) sebacate, bis(1-(2-hydroxy-2-methylpropoxy)-2,2,6,6-tetramethylpiperidin-4-yl)adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl) glutarate and 2,4-bis{N-[1-(2-hydroxy-2-methylpropoxy)-2,2,6,6-tetramethylpiperidin-4-yl]-N-butylamino}-6-(2-hydroxyethylamino)-s-triazine.

2.8. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.9. Tris-aryl-o-hydroxyphenyl-s-triazines, for example known commercial tris-aryl-o-hydroxyphenyl-s-triazines and triazines as disclosed in, WO 96/28431, EP 434608, EP 941989, GB 2,317,893, U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,942,626; 5,959,008; 5,998,116 and 6,013,704, for example 4,6-bis-(2,4-dimethylphenyl)-2-(2-hydroxy-4-octyloxyphenyl)-s-triazine, 4,6-bis-(2,4-dimethylphenyl)-2-(2,4-dihydroxyphenyl)-s-triazine, 2,4-bis(2,4-dihydroxyphenyl)-6-(4-chlorophenyl)-s-triazine, 2,4-bis[2-hydroxy-4-(2-hydroxy-ethoxy)phenyl]-6-(4-chlorophenyl)-s-triazine, 2,4-bis[2-hydroxy-4-(2-hydroxy-4-(2-hydroxy-ethoxy)phenyl]-6-(2,4-dimethylphenyl)-s-triazine, 2,4-bis[2-hydroxy-4-(2-hydroxyethoxy)-phenyl]-6-(4-bromophenyl)-s-triazine, 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine, 2,4-bis(4-biphenylyl)-6-(2-hydroxy4-octyloxycarbonylethylideneoxyphenyl)-s-triazine, 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)phenyl]-s-triazine, 2,4-bis(2,4-dimethylphenyl)-6-[2-hydroxy4-(3-benzyloxy-2-hydroxypropyloxy)phenyl]-s-triazine, 2,4-bis(2-hydroxy-4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-α-cumylphenyl]-s-triazine (* denotes a mixture of octyloxy, nonyloxy and decyloxy groups), methylenebis-{2,4-bis(2,4-dimethylphenyl)-6-[2-hydroxy4-(3-butyloxy-2-hydroxypropoxy)phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonyliso-propylideneoxyphenyl)-s-triazine, 2,4-bis(2,4-dimethylphenyl)-6-(2-hydroxy-4-hexyloxy-5-α-cumylphenyl)-s-triazine, 2-(2,4,6-trimethylphenyl)4,6-bis[2-hydroxy-4-(3-butyloxy-2-hydroxy-propyloxy) phenyl]-s-triazine, 2,4,6-tris[2-hydroxy-4-(3-sec-butyloxy-2-hydroxypropyloxy)-phenyl]-s-triazine, mixture of 4,6-bis-(2,4-dimethylphenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, 4,6-bis-(2,4-dimethylphenyl)-2-(2-hydroxy-4-(3-(2-ethylhexyloxy)-2-hydroxypropoxy)-phenyl)-s-triazine and 4,6-diphenyl-2-(4-hexyloxy-2-hydroxyphenyl)-s-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-dibenzo[d,f][1,3,2]dioxaphosphepin, 6-fluoro-2,4,8,10-tetra-tert-butyl-12-methyl-dibenzo[d,g][1,3,2] dioxaphosphocin, bis(2,4-di-tert-butyl-6-methylphenyl) methyl phosphite, bis(2,4-di-tert-butyl-6-methylphenyl) ethyl phosphite, 2,2',2''-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite.

5. Benzofuranones and indolinones, for example those disclosed in U.S. Pat. Nos. 4,325,863, 4,338,244, 5,175,312, 5,216,052, 5,252,643; DE-A-4316611; DE-A-4316622; DE-A-4316876; EP-A-0589839 or EP-A-0591102 or 3-[4-(2-acetoxyeth-oxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, and 3-(2,3-dimethylphenyl)-5,7-di-tert-butyl-benzofuran-2-one.

6. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N-methyl-N-octadecylhydroxylamine and the N,N-dialkylhydroxylamine derived from hydrogenated tallow amine.

7. Nitrones, for example N-benzyl-α-phenylnitrone, N-ethyl-α-methylnitrone, N-octyl-α-heptylnitrone, N-lauryl-α-undecylnitrone, N-tetradecyl-α-tridcylnitrone, N-hexadecyl-α-pentadecylnitrone, N-octadecyl-α-heptadecylnitrone, N-hexadecyl-α-heptadecylnitrone, N-octadecyl-α-pentadecylnitrone, N-heptadecyl-α-heptadecylnitrone, N-octadecyl-α-hexadecylnitrone, N-methyl-α-heptadecylnitrone and the nitrone derived from N,N-dialkylhydroxylamine derived from hydrogenated tallow amine.

8. Amine oxides, for example amine oxide derivatives as disclosed in U.S. Pat. Nos. 5,844,029 and 5,880,191, didecyl methyl amine oxide, tridecyl amine oxide, tridodecyl amine oxide and trihexadecyl amine oxide.

9. Thiosynergists, for example dilauryl thiodipropionate or distearyl thiodipropionate.

10. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

11. Polyamide stabilizers, for example copper salts in combination with iodides and/or phosphorus compounds and salts of divalent manganese.

12. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zinc pyrocatecholate.

13. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

14. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

15. Dispersing Agents, such as polyethylene oxide waxes or mineral oil.

16. Other additives, for example plasticizers, lubricants, emulsifiers, pigments, dyes, other optical brighteners, rheology additives, catalysts, flow-control agents, slip agents, crosslinking agents, crosslinking boosters, halogen scavengers, smoke inhibitors, flameproofing agents, antistatic agents, clarifiers such as substituted and unsubstituted bisbenzylidene sorbitols, benzoxazinone UV absorbers such as 2,2'-p-phenylene-bis(3,1-benzoxazin-4-one), and blowing agents.

Colorants, e.g., dyes and pigments, are frequently present in compositions comprising the present FWAs.

For example, a pigment composition comprising the present FWAs is prepared by blending the pigment with a compound of formula (I) or (II) to provide a toner which can be used in the production of, for example, paints and other coatings, inks and other printing materials or the toner could be incorporated in to other articles or formulations. Compositions comprising the toner would fluoresce under UV light.

The present FWAs can also be blended into compositions comprising pigments or dyes in conventional ways without prior blending to produce a toner. Compositions comprising a FWA of the present invention and a pigment and/or dye, with or without prior blending, are suitable for printing inks that provide quick identification, security and protection against forgery.

Compounds of formula (I) or (II) may be incorporated into packaging inks as a promotional tool or as a tracer for packaging lines or into primer and/or topcoats for use as a marker to identify voids or uneven coverage.

Compounds of formula (I) or (II) may be incorporated during the manufacture of fluorescent dyes or pigments.

Compounds of formula (I) or (II) may be incorporated into dyes or pigments to reinforce the brightness of certain shades, for example blue tones; to increase the deep tone of colors, for example, those found in black or blue printing inks; to intensify the degree of whiteness in white or pastel shades.

Compounds of formula (I) or (II) may be incorporated into polymer resins according to known methods to provide many of the advantages described above. For example, the compounds may be added as an individual component during blending, for example, dry blending of the resin prior to prior to processing, or the compound may be added as a blend, master batch, flush, or other concentrate in another substance prior to processing. The compounds may also be added during processing steps. Standard process steps for polymer resins are well known in the literature and include extrusion, coextrusion, Brabender melt processing, film formation, injection molding, blow molding, other molding and sheet forming processes, fiber formation etc.

The compounds of formula (I) or (II) are also incorporated via suspension and dispersion methods.

When used in a coating, ink, polish, wax or paint formulation, the said formulation may be applied to any compatible organic or inorganic substrate.

When used for the fluorescent whitening of paper, a fluorescent whitening agent comprising compounds of formula (I) or (II) and, optionally, auxiliaries, may be applied to the paper substrate in the pulp mass, in the form of a paper coating composition, or directly in the size press or metering press.

For example, they are used in the production or coating of white or colored paper and paper products.

Suitable auxiliaries include, for example, anionic or non-ionic dispersants from the class of ethylene oxide adducts fatty alcohols, higher fatty acids or alkyl phenols or ethylenediamine ethylene oxide-propylene oxide adducts, copolymers of N-vinylpyrrolidone with 3-vinylpropionic acid, water retention aids, e.g., ethylene glycol, glycerol or sorbitol, or biocides.

The paper coating compositions may contain, as binder, plastics dispersions based on copolymers of butadiene/styrene, acrylonitrile/butadiene/styrene, acrylic acid esters, acrylic acid esters/styrene/acrylonitrile, ethylene/vinyl chloride and ethylene/vinyl acetate; or homopolymers, such as polyvinyl chloride, polyvinylidene chloride, polyethylene and polyvinyl acetate or polyurethanes.

For example, the paper coating composition is used to produce coated printed or writing paper, or special papers such as ink-jet or photographic papers, or cardboard.

The paper coating composition used according to the method of the invention can be applied to the substrate by any conventional process, for example with an air blade, a coating blade, a roller, a doctor blade or a rod, or in the size press.

Compositions comprising the compounds of formula (I) or (II) are excellent fluorescent whitening agents for substrates such as textiles and for the addition to detergent compositions.

A further aspect of the invention provides a method for increasing the SPF (Sun Protection Factor) rating or for the fluorescent whitening of a textile fiber material, comprising treating the textile fiber material with 0.05 to 10.0% by weight, for example 0.1 to 5.0% by weight, based on the weight of the textile fiber material, with a compound of formula (I) or (II).

The method of the present invention, in addition to providing protection to the skin, also increases the useful life of a textile article treated according to the present invention. For example, the tear resistance and/or light fastness of the treated textile fiber material may be improved.

Such textile fabrics and articles of clothing produced from the said fabrics typically have an SPF rating of 15 and above, whereas untreated cotton, for example, generally has an SPF rating of from 2 to 4.

The amount of FWA of the present invention used in an application will vary greatly depending on the end use and effect desired. Typical load levels of known FWAs are well know to the practitioner or are readily found in the literature and would be adequate starting points for those formulating with the present FWAs. Solid particle FWAs may find use in slightly higher concentrations than soluble FWAs.

For example, to mask yellowness in non-colored PVC, polystyrene and polycarbonate, FWA load levels of between about 50 ppm to about 500 ppm or more are common. Ultra white polyurethanes, for example, may need 500 ppm or more of FWA. Other applications, for example, where the FWA is also intended to be used a UV screening agent, may require much higher amounts of UVA, for example, some textile applications may be made of fibers containing between about 0.05% to about 10% FWA based on total weight of the fiber. For example, toners may comprise roughly equal amounts of pigment and FWA. Dispersions for paper whitening may comprise from about 5% to about 60% FWA by weight based on total weight of dispersion. Finished paper may comprise as little as 1 ppm FWA.

The FWA of the present invention can therefore be used in almost any concentration depending on the end use application.

Other applications for the compounds of the present invention will be apparent to those skilled in the art and the invention is not limited to the applications disclosed herein.

EXAMPLES

The following Examples serve to illustrate the invention without intending to be restrictive in nature; parts and percentages are by weight, unless otherwise stated.

Example 1

5,7,12,14-tetrahydro[4,3-j]quinophenanthrine-6,13-dione

To a stirred solution of 25 grams of dimethyl succinylsuccinate, 210 grams of a high boiling aromatic-ether based solvent and ~5 drops of water at 90° C. in a round bottom flask equipped with reflux condenser, thermocouple, overhead agitator and drying tube under nitrogen is added 25 mL of aniline. The resulting mixture is heated to 160° C. and held for three hours to form a white precipitate. The reaction mixture is filtered hot (~125° C.), the precipitate is washed with 100 mL hot solvent (same as reaction solvent), the presscake is washed with 1 L methanol to yield, after drying in a vacuum oven at 80° C., 22.4 grams of dianilino-cyclohexane-1,4-dione-2,5-dicarboxylate as a white solid, mp 250-251° C.; proton nmr (500 MHz, $D_2SO_4$) δ 3.36 ppm (s, 4H), 7.1 ppm (d, 4H), 7.2 ppm (m, 6H).

To 320 grams of polyphosphoric acid stirred at 105° C. in a round bottom flask equipped with reflux condenser, thermocouple, overhead agitator and drying tube under nitrogen is added 7 grams of dianilino-cyclohexane-1,4-dione-2,5-dicarboxylate. The resulting yellow solution is heated to 140-160° C. and held for two hours after which the reaction is opened to air and heated to 190-195° C. during which time the reaction mixture turns orange. After holding at 190-195° C. for 0.5 hr the reaction mixture is cooled to 85° C. and 20 mL of water is added dropwise over 5 minutes with an exotherm. After cooling to 100 ° C., the reaction mixture is poured into 500 grams of water at room temperature, heated at 60-65° C. for 0.5 hr with agitation and filtered. The solid is washed with warm water until a pH of 6.5 or higher is reached to yield, after drying at 80° C., 3.5 grams of 5,7,12,14-tetrahydro[4,3-j]quinophenanthrine-6,13-dione (TPQA) as a pale yellow solid mp 289-300° C. (dec) which can be recrystallized from concentrated sulfuric acid to yield a pale yellow solid; proton nmr (500 MHz, $D_2SO_4$) δ 4.38 ppm (s, 4H), 7.55 ppm (t, 2H), 7.71 ppm (t, 2H), 8.0 ppm (d, 2H).

Example 2

2,9-dimethyl-5,7,12,14-tetrahydro[4,3-j]quinophenanthrine-6,13-dione is prepared as a yellow solid following the general procedure of Example 1 using p-toluidine in place of aniline The following are prepared following the general procedure of Example 1 using the appropriate aniline derivative or mixtures of aniline derivatives. The use of mixtures of aniline derivatives yields a mixture of symmetrical and unsymmetrical compounds which are used as a mixture or separated.

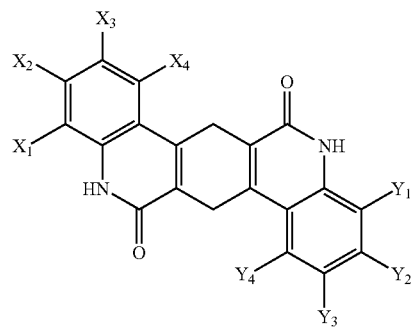

| Example | X1 | X2 | X3 | X4 | Y1 | Y2 | Y3 | Y4 |
|---|---|---|---|---|---|---|---|---|
| 3 | $CH_3$ | H | H | H | $CH_3$ | H | H | H |
| 4 | H | $CH_3$ | H | H | H | $CH_3$ | H | H |
| 5 | H | H | $t-C_4H_9$ | H | H | H | $t-C_4H_9$ | H |
| 6 | $CH_3$ | H | $CH_3$ | H | $CH_3$ | H | $CH_3$ | H |
| 7 | H | $CH_3$ | $CH_3$ | H | H | $CH_3$ | $CH_3$ | H |

-continued

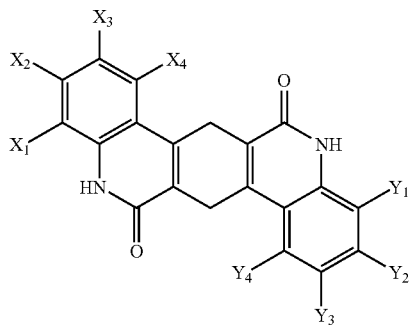

| Example | X1 | X2 | X3 | X4 | Y1 | Y2 | Y3 | Y4 |
|---|---|---|---|---|---|---|---|---|
| 8 | CH₃ | H | H | H | H | H | H | H |
| 9 | H | CH₃ | H | H | H | H | H | H |
| 10 | H | H | CH₃ | H | H | H | H | H |
| 11 | CH₃ | H | CH₃ | H | H | H | H | H |
| 12 | H | CH₃ | CH₃ | H | H | H | H | H |
| 13 | Cl | H | H | H | Cl | H | H | H |
| 14 | H | Cl | H | H | H | Cl | H | H |
| 15 | H | H | Cl | H | H | H | Cl | H |
| 16 | Cl | H | Cl | H | Cl | H | CL | H |
| 17 | H | Cl | Cl | H | H | Cl | Cl | H |
| 18 | Cl | Cl | Cl | Cl | Cl | Cl | Cl | Cl |
| 19 | H | H | H | H | Cl | H | H | H |
| 20 | H | H | H | H | H | Cl | H | H |
| 21 | H | H | H | H | H | H | Cl | H |
| 22 | H | H | H | H | Cl | H | CL | H |
| 23 | H | H | H | H | H | Cl | Cl | H |
| 24 | H | H | H | H | Cl | Cl | Cl | Cl |
| 25 | H | H | CH₃ | H | H | H | Cl | H |
| 26 | CH₃ | H | Cl | H | CH₃ | H | Cl | H |
| 28 | H | CH₃ | CH₃ | H | H | Cl | Cl | H |

Example 29

5,12-dihydro[4,3-j]quinophenanthrine-6,13-dione is prepared by oxidizing the product of Example 1

Example 30

2,9-dimethyl-5,12,-dihydro[4,3-j]quinophenanthrine-6,13-dione is prepared by oxidizing the product of Example 2

The following are prepared by following the general procedure of Example 1 using the appropriate aniline derivative or mixtures of aniline derivatives and then oxidizing the resulting product. The use of mixtures of aniline derivatives yields a mixture of symmetrical and unsymmetrical compounds which are used as a mixture or separated.

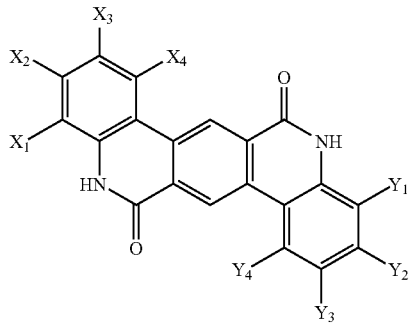

| Example | X1 | X2 | X3 | X4 | Y1 | Y2 | Y3 | Y4 |
|---|---|---|---|---|---|---|---|---|
| 31 | CH₃ | H | H | H | CH₃ | H | H | H |
| 32 | H | CH₃ | H | H | H | CH₃ | H | H |
| 33 | H | H | t-C₄H₉ | H | H | H | t-C₄H₉ | H |
| 34 | CH₃ | H | CH₃ | H | CH₃ | H | CH₃ | H |
| 35 | H | CH₃ | CH₃ | H | H | CH₃ | CH₃ | H |
| 36 | CH₃ | H | H | H | H | H | H | H |
| 37 | H | CH₃ | H | H | H | H | H | H |
| 38 | H | H | CH₃ | H | H | H | H | H |
| 39 | CH₃ | H | CH₃ | H | H | H | H | H |
| 40 | H | CH₃ | CH₃ | H | H | H | H | H |
| 41 | Cl | H | H | H | Cl | H | H | H |
| 42 | H | Cl | H | H | H | Cl | H | H |
| 43 | H | H | Cl | H | H | H | Cl | H |
| 44 | Cl | H | Cl | H | Cl | H | CL | H |
| 45 | H | Cl | Cl | H | H | Cl | Cl | H |
| 46 | Cl | Cl | Cl | Cl | Cl | Cl | Cl | Cl |
| 47 | H | H | H | H | Cl | H | H | H |
| 48 | H | H | H | H | H | Cl | H | H |
| 49 | H | H | H | H | H | H | Cl | H |
| 50 | H | H | H | H | Cl | H | CL | H |
| 51 | H | H | H | H | H | Cl | Cl | H |
| 52 | H | H | H | H | Cl | Cl | Cl | Cl |
| 53 | H | H | CH₃ | H | H | H | Cl | H |
| 54 | CH₃ | H | Cl | H | CH₃ | H | Cl | H |
| 55 | H | CH₃ | CH₃ | H | H | Cl | Cl | H |

Example 56

Fluorescent Toner Composition

A composition comprising 89.8 grams of a 33.6% 2,9-dichloroquinacridone/quinacridone solid solution presscake is blended with 34.4 g of a 5.4% press-cake of the TPQA product of Example 1. The resulting mixture is dried to form a toner.

Example 57

Fluorescent Coating Composition

A mixture of 2.3 grams of the toner of Example 2, 1.2 grams of DISPERBYK 161, 16.9 grams of a mill base and 39.3 grams of a letdown is milled with 100 grams of 2 mm glass beads using a SKANDEX mill. The resulting paint is separated from the beads.

A drawdown of the paint using a 100 micron wet film wired bar and a KCC automatic film applicator is prepared and dried and compared to a similar drawdown prepared from a paint which differs only by not containing the TPQA product of Example 1. The paints appear to be identical under ambient lighting, however, the paint comprising the toner from Example 2 fluoresces under a black white, the paint without the TPQA product of Example 1 does not fluoresce under a black light.

The compounds of the present invention are active in fluorescent colored materials.

Example 58

A mixture of 90 grams of a paste containing 6 grams of the TPQA product of Example 1, 54 grams of AC6A polyethylene wax and ~300 grams of water are pebble milled for 20 hours. The mixture is filtered and dried at 80° C. overnight. 12 grams of the FWAtwax mixture and 588 grams of dried nylon 6 are compounded using a single screw extruder at 470° F. The resulting material is formed into chips by injection molding. The chips are further processed into fiber, plaques and other molded articles using conventional means.

The compounds of the present invention are stable at high processing temperatures.

The invention claimed is:

1. A fluorescent whitening agent of formula (I) or (II)

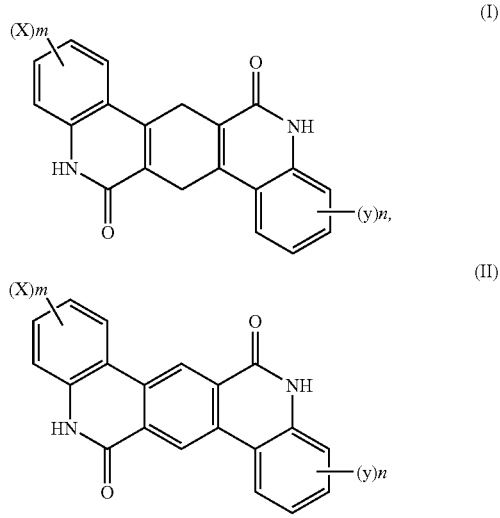

wherein

X and Y, independently of each other are $C_{1-12}$ straight or branched chain alkyl, $C_{3-6}$ cycloalkyl, $C_{6-10}$ aromatic, $C_{3-9}$ saturated or unsaturated heterocycle, $C_{7-12}$ aralkyl, halogen, —OR, $CF_3$, —COOR, —CONR'R, $NO_2$, NR'R, $SO_3H$, $SO_2NR'R$ or $C_{2-8}$ alkylcarbonyl, R and R', independently of each other are hydrogen, $C_{1-8}$ straight or branched chain alkyl, $C_{3-6}$ cycloalkyl, $C_{6-10}$ aromatic, $C_{7-12}$ aralkyl or $C_{2-8}$ alkylcarbonyl, and m and n are independently 0, 1, 2, 3 or 4, when m or n is 2, 3 or 4, each X or Y substituent may be a different group as defined above with the proviso that m and n are not simultaneously 0.

2. A fluorescent whitening agent according to claim 1, wherein X and Y, independently of each other are $C_{1-8}$ straight or branched chain alkyl, $C_{5-6}$ cycloalkyl, $C_{6-10}$ aromatic, pyridine, $C_{7-12}$ aralkyl, halogen, —OR, $CF_3$, —COOR, —CONR'R, $NO_2$, NR'R, $SO_3H$ or $SO_2NR'R$, R and R', independently of each other are $C_{1-8}$ straight or branched chain alkyl, $C_{5-6}$ cycloalkyl, $C_{6-10}$ aromatic, $C_{7-12}$ aralkyl, acetyl or propionyl, and m and n are independently 0, 1 or 2, when m or n is 2 each X or Y substituent may be a different group as defined above.

3. A fluorescent whitening agent according to claim 2, wherein X and Y, independently of each other are F, Cl, Br, $C_{1-8}$ straight or branched chain alkyl, cyclohexyl, phenyl, naphthyl, benzyl, cumyl, —OH, $OC_{1-4}$alkyl, $CF_3$, —$COOC_{1-8}$alkyl, —CONR'R, $NO_2$, NR'R or $SO_3H$, and R and R', independently of each other are hydrogen, $C_{1-4}$ straight or branched chain alkyl, phenyl, benzyl or cumyl.

4. A fluorescent whitening agent according to claim 1, wherein, X and Y, independently of each other are Cl, $C_{1-4}$ straight or branched chain alkyl, $OC_{1-4}$alkyl, and m and n are independently 0 or 1.

5. A fluorescent whitening agent according to claim 1, wherein X and Y are the same.

6. A fluorescent whitening agent according to claim 1, wherein X and Y are different.

7. A process for preparing a fluorescent whitening agent according to claim 1, wherein reaction of a di-$C_{1-12}$alkyl succinylsuccinate and an aniline derivative to form a dianiline amide of cyclohexane-1,4-dione-2,5-dicarboxylate is followed by cyclization, dehydration and optionally aromatization.

8. A process for preparing a fluorescent whitening agent according to claim 7, wherein cyclization and dehydration are performed in a single pot process.

9. A process for preparing a fluorescent whitening agent according to claim 8, wherein the dianiline amide of cyclohexane-1,4-dione-2,5-dicarboxylate is treated with polyphosphoric acid.

10. A fluorescent whitening agent of formula (I) according to claim 1.

11. A fluorescent whitening agent of formula (I) according to claim 1 wherein, X and Y, independently of each other are Cl, $C_{1-4}$ straight or branched chain alkyl, $OC_{1-4}$alkyl, and m and n are independently 0 or 1.

12. A composition comprising a natural or synthetic polymer and a fluorescent whitening agent according to claim 1.

13. A composition according to claim 12, wherein the natural polymer is paper, cotton, viscose, flax, rayon, linen, wool, cashmere, angora, silk, cellulose, natural rubber or gelatin.

14. A composition according to claim 12, wherein the polymer is a synthetic thermoplastic, thermoset or elastomeric polymer, or crosslinked thermoplastic, thermoset or elastomeric polymer.

15. A composition according to claim 14, wherein the synthetic polymer is a polyolefin, polyamide, polyurethane, polyacrylate, polyacrylamide, polyvinyl alcohol, polycarbonate, polystyrene, polyester, polyacetal or a halogenated vinyl polymer.

16. A composition according to claim 12 which is a film, injection moulded article, thermoset article, coating, extruded workpiece, fiber, sheet, or fabric.

17. A composition according to claim 16, wherein the coating is an auto coating, paint, stain, laminate or receiving layer for printing application.

18. A fluorescent toner or ink comprising a fluorescent whitening agent according to claim 1.

19. A cosmetic formulation, detergent, wax or polish comprising a fluorescent whitening agent according to claim 1.

* * * * *